United States Patent [19]
Cote et al.

[11] Patent Number: 5,431,672
[45] Date of Patent: Jul. 11, 1995

[54] SURGICAL SCALPEL WITH RETRACTABLE BLADE

[75] Inventors: Dana M. Cote, Billerica; Thomas H. Doucette, Stow; John Mazzola, Harvard, all of Mass.

[73] Assignee: Becton, Dickinson and Company, Franklin Lakes, N.J.

[21] Appl. No.: 239,666

[22] Filed: May 9, 1994

[51] Int. Cl.⁶ .................................................. A61B 17/32
[52] U.S. Cl. ........................................ 606/167; 30/2; 30/167
[58] Field of Search ............... 606/166, 167, 172, 181, 606/182, 185; 30/2, 151, 162, 164, 167, 286, 335, 339

[56] References Cited

U.S. PATENT DOCUMENTS

| | | |
|---|---|---|
| 1,434,388 | 11/1922 | Hughes . |
| 2,735,176 | 2/1956 | Costin . |
| 3,905,101 | 9/1975 | Shepherd . |
| 3,906,626 | 9/1975 | Riuli . |
| 4,713,885 | 12/1987 | Keklak et al. ............... 30/162 |
| 4,823,457 | 4/1990 | Prochaska . |
| 5,201,748 | 4/1993 | Newman et al. ............ 606/167 |
| 5,207,696 | 5/1993 | Matwijcow ................. 606/167 |
| 5,222,951 | 6/1993 | Abidin et al. ................ 30/162 |
| 5,275,606 | 1/1994 | Abidin et al. ............... 606/167 |
| 5,292,329 | 3/1994 | Werner ........................ 30/162 |
| 5,303,474 | 4/1994 | Keklak et al. ................ 30/162 |

*Primary Examiner*—Stephen C. Pellegrino
*Assistant Examiner*—William W. Lewis
*Attorney, Agent, or Firm*—Alan W. Fiedler; Eric M. Lee

[57] ABSTRACT

A surgical scalpel having a handle with a blade carrying carriage that can be slid from an intermediate position where the blade is within the handle to an extended position where the blade extends beyond the distal end of the handle and is exposed for use. After use, the blade can then be slid back to the intermediate position to cover the blade when being passed between operating room personnel or can be slid to a permanently locked position where the blade is permanently covered permitting the scalpel to be disposed of. In addition, means are provided for securely latching the blade in the extended position and the intermediate position to prevent inadvertent movement of the blade and means are provided for indicating that the blade is in the permanently locked position for disposal.

15 Claims, 7 Drawing Sheets

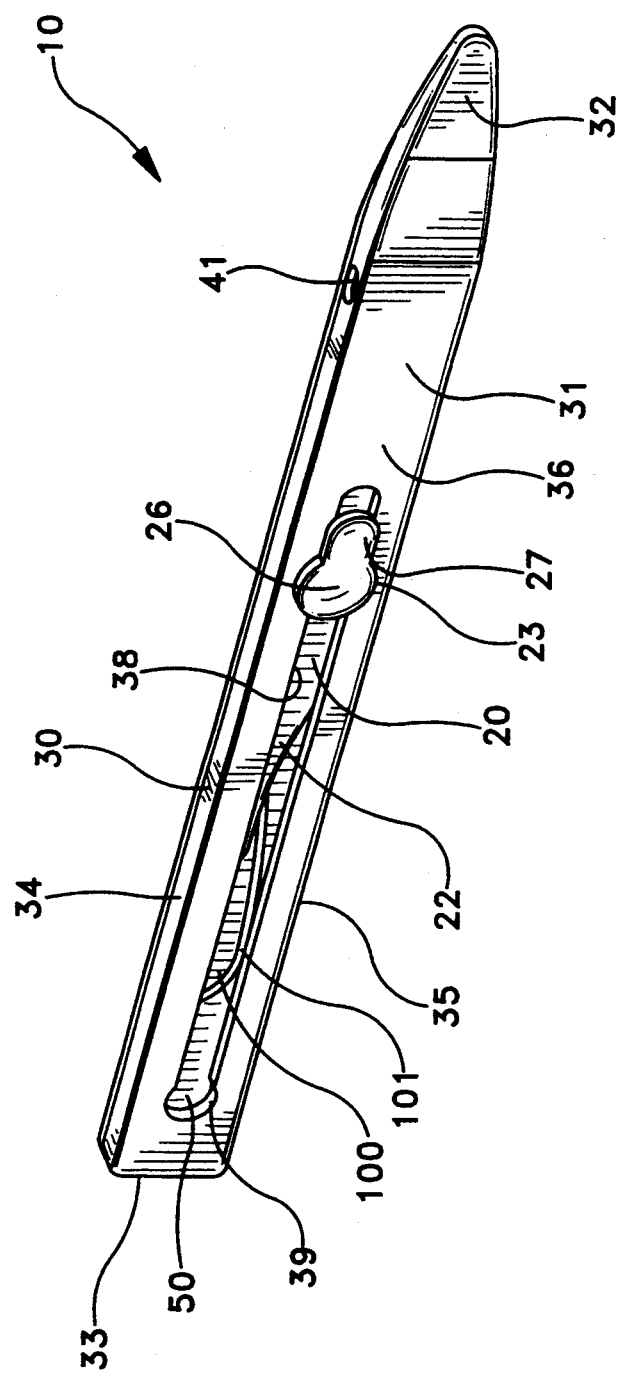
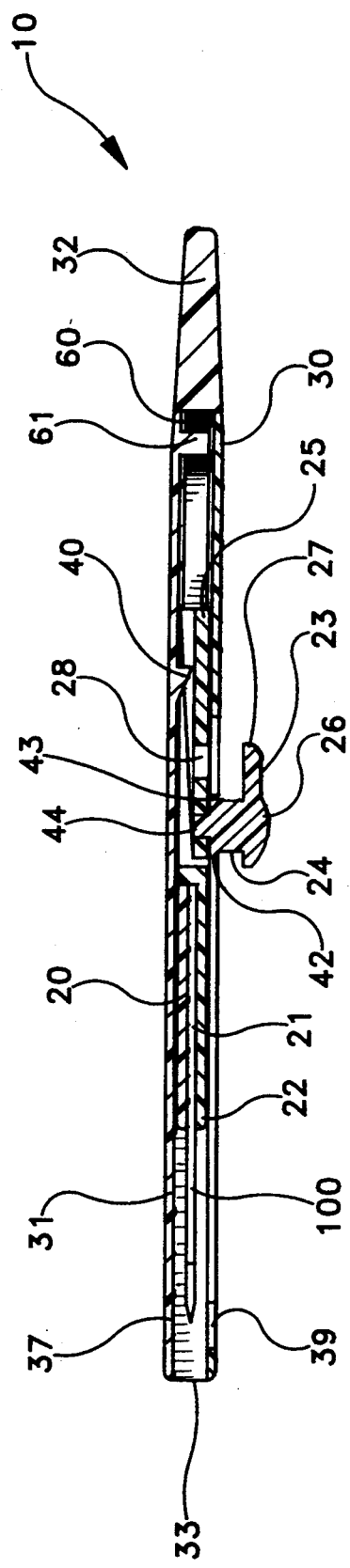
FIG-1
FIG-2

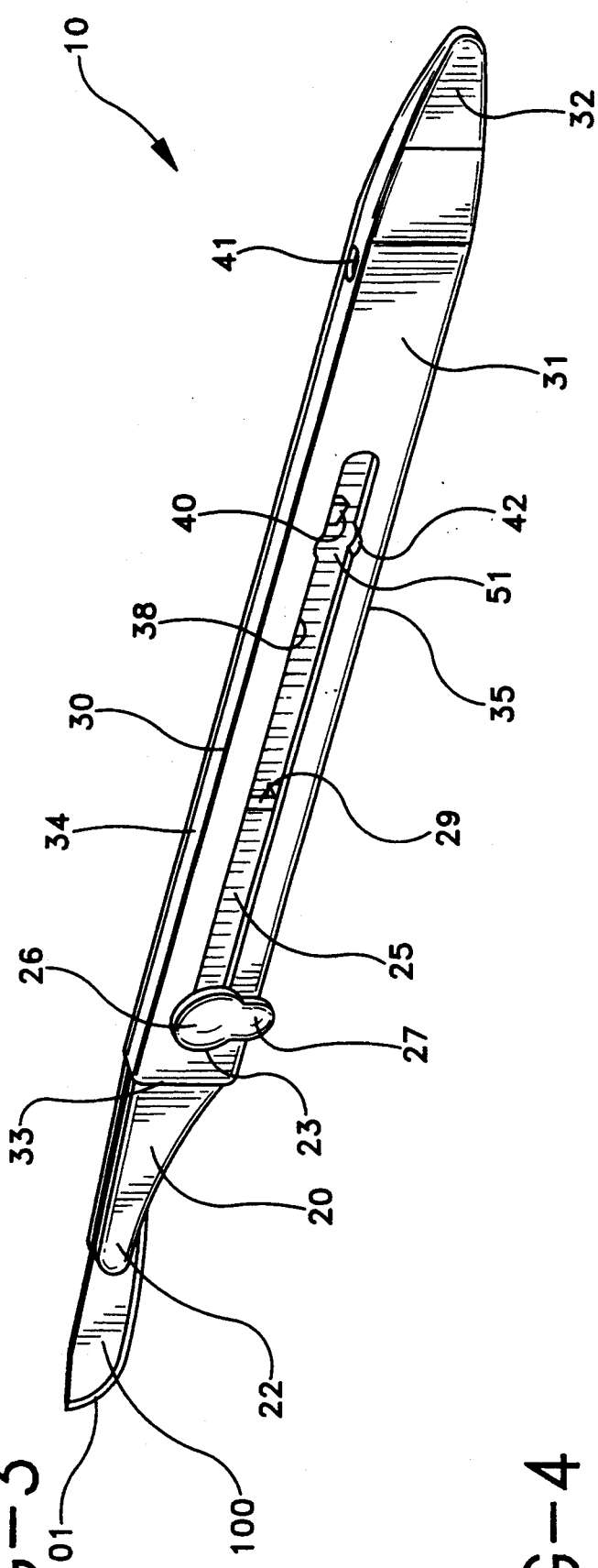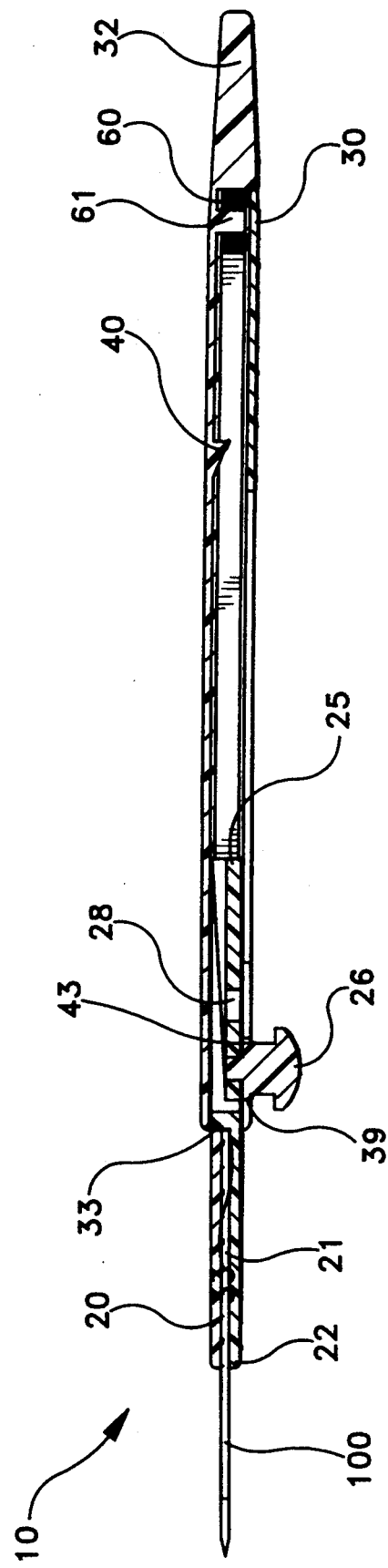

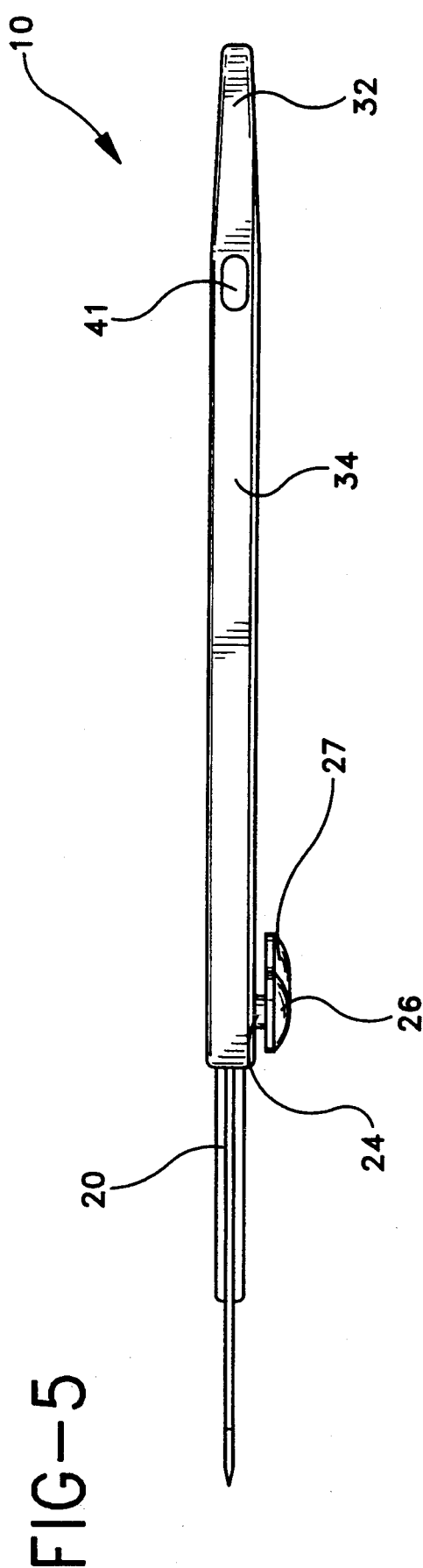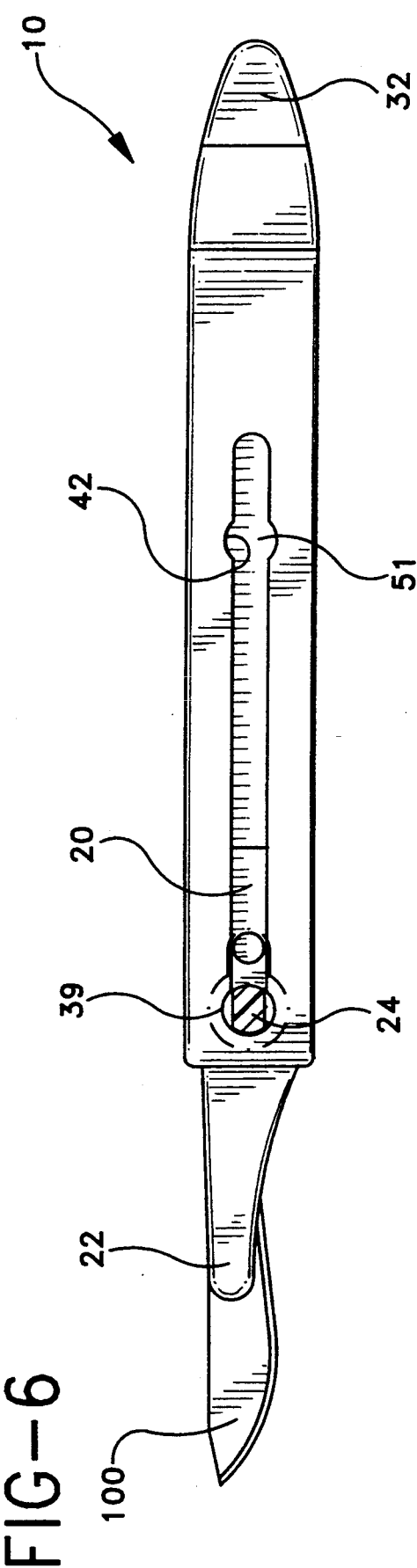

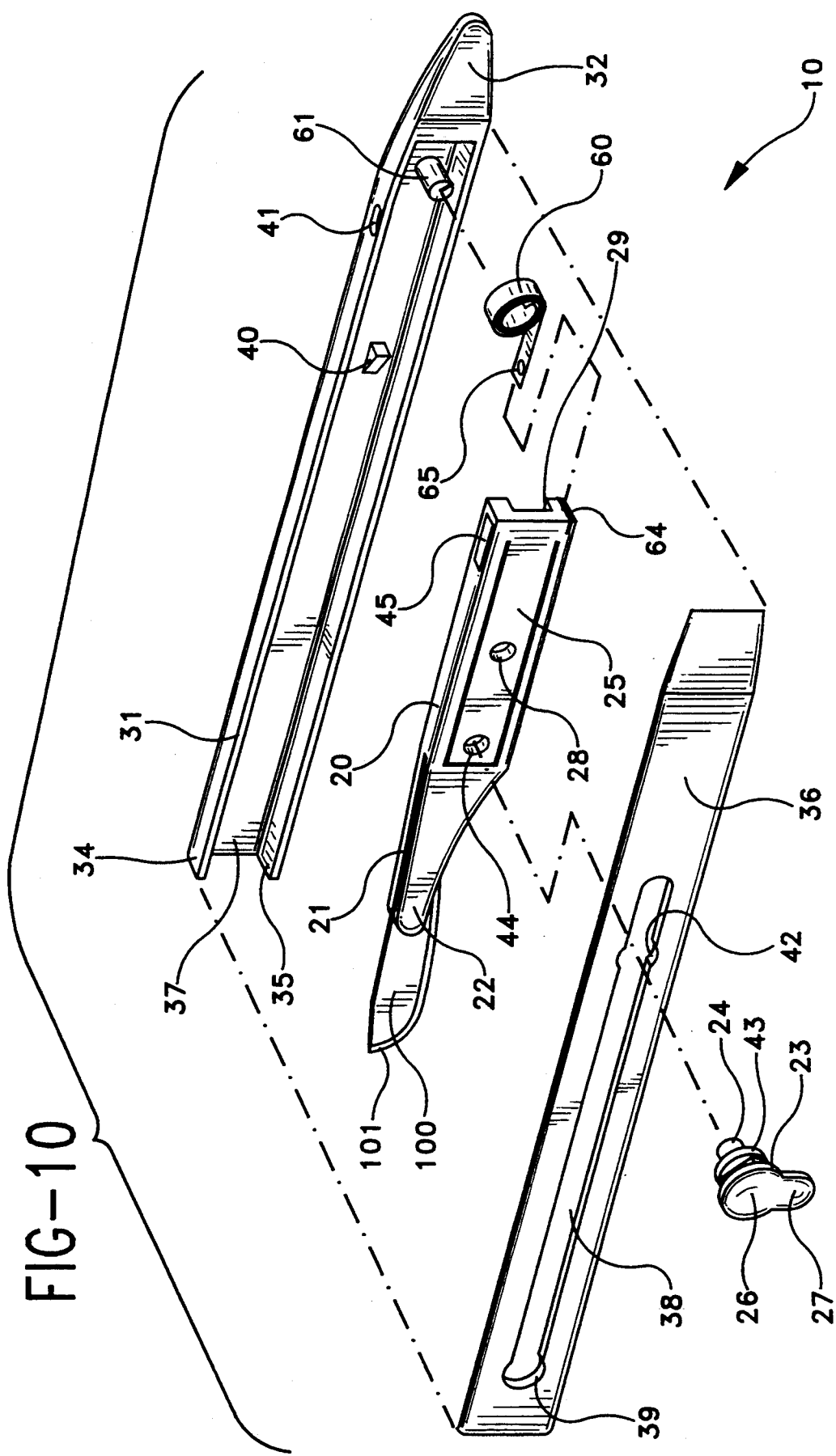

SURGICAL SCALPEL WITH RETRACTABLE BLADE

BACKGROUND OF THE INVENTION

1. Field of the Invention

The present invention relates to a surgical scalpel and, more particularly, relates to a surgical scalpel having a retractable blade that slides from an intermediate position to an extended position and finally to a permanently retracted position for disposal.

2. Background Description

As practitioners-in-the-art of surgery are aware, it has long been a goal to have a scalpel with a blade that is guarded from inadvertent contact before and after use with means for insuring that the blade will stay in the extended position during use and means for easily and permanently locking the blade in a position for disposal purposes.

An example of a guarded scalpel is shown in U.S. Pat. No. 3,906,626 (Riuli). The scalpel in Riuli is disposable and has a slidable sheath that temporarily covers the blade of the scalpel when the scalpel is not in use and permanently covers the blade when the scalpel is to be disposed of. However, there is no means for insuring that the blade will remain extended during use or means for indicating that the blade is permanently locked within the guard.

SUMMARY OF THE INVENTION

The present invention overcomes the problems identified in the background material by providing a surgical scalpel having a blade that can be slid from an intermediate position to an extended position during use and then to a permanently locked and guarded position after use.

A preferred embodiment of the surgical scalpel includes a handle with a blade that can be slid from an intermediate position where the blade is within the handle to an extended position where the blade extends beyond the end of the handle and is exposed for use. The blade can then be slid back to the intermediate position to cover the blade when being passed, and can be moved to a permanently locked position so that the blade is permanently covered and can be disposed of. In addition, means are provided for easily locking the blade in the extended and intermediate positions to prevent inadvertent movement of the blade and means are provided for indicating when the blade is in the permanently locked position.

These and other aspects, features and advantages of the present invention will become apparent from the following detailed description taken in conjunction with the accompanying drawings.

DESCRIPTION OF THE DRAWINGS

FIG. 1 is an isometric view of a preferred surgical scalpel of the present invention, with a slidable blade in an intermediate position within a handle;

FIG. 2 is a cross-sectional view of the surgical scalpel shown in FIG. 1;

FIG. 3 is an isometric view of the surgical scalpel shown in FIG. 1, with the blade in an extended and latched position;

FIG. 4 is a cross-sectional view of the surgical scalpel in the extended and latched position, shown in FIG. 3;

FIG. 5 is a top view of the surgical scalpel shown in FIG. 3, with the blade in an extended and unlatched position;

FIG. 6 is a side view of the surgical scalpel in the extended and unlatched position, shown in FIG. 5;

FIG. 10 is an exploded isometric view of the surgical scalpel shown in FIG. 1; and.

DETAILED DESCRIPTION

Figure 7:
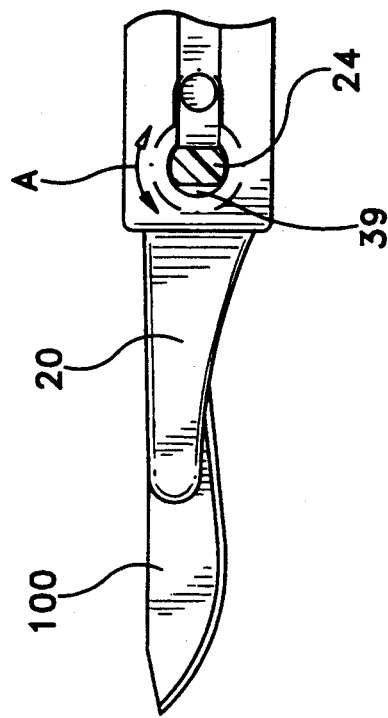
FIG. 7 is a side view of the front portion of the surgical scalpel shown in FIGS. 3–6, showing the operation of the button when latching and unlatching the blade in the extended position.

A preferred surgical scalpel 10 embodying the principles and concepts of the present invention is shown in FIGS. 1–10. Scalpel 10 includes a carriage 20 that is slidably mounted within a handle portion 30 for movement from an intermediate position shown in FIGS. 1 and 2, to an extended position shown in FIGS. 3–7, and finally to a permanently locked retracted position for disposal shown in FIGS. 8 and 9.

FIGS. 1 and 2 are an isometric view and a cross-sectional view, respectively, of a preferred surgical scalpel of the present invention, with a slidable blade carrying carriage 20 in an intermediate position within a handle 30. As shown in FIGS. 1 and 2, carriage 20 includes a blade 100 mounted to a tapered distal end 22 of carriage 20 within a slot 21. Distal end 22 is tapered to provide improved access to a curing surface 101 on blade 100 during use. It should be appreciated, however, that slot 21 is merely exemplary since other means of attaching blade 100 to carriage 20 could also be used, e.g., using a boss to mechanically, chemically or ultrasonically hold blade 100, and still remain within the scope of the present invention. Carriage 20 also includes a resilient and rotatably mounted button 26 having a head 23 with a tab 27 extending therefrom, button 26 being rotatably fastened by a post 24 to a port 44 in a flexible portion 25 on carriage 20 and rotatable by the user pushing on tab 27. Flexible portion 25 provides the resiliency for button 26 and receives post 24 so that the entire post 24 and button 26 assembly can freely rotate. As shown in FIG. 2, post 24 includes a shoulder 43 that surrounds post 24 and is located between button 26 and flexible portion 25.

Handle portion 30 includes an elongated housing 31 with a tapered butt 32 at its proximal end and an opening 33 at its distal end. Housing 31 is defined by a top surface 34, a bottom surface 35 and a second side wall 37, and is closed by a first side wall 36. First side wall 36 includes a longitudinal slot 38 having a first enlarged opening 39 at a distal end 50 and a second enlarged opening 42 spaced from a proximal end 51 for receiving shoulder 43 on post 24. Top surface 34 near the proximal end of housing 31 includes a view port 41 for displaying whether blade 100 is or is not in the permanently locked retracted position shown in FIGS. 8 and 9, discussed below. In addition, housing 31 includes a coil spring 60 mounted on a spring support 61 and attached in a mounting slot 64, shown in FIG. 10, to the proximal end of carriage 20 by a pin (not shown) and a hole 65 in coil spring 60. Coil spring 60 provides means for retracting carriage 20 into housing 31, since it compresses as it unwinds to the extended position shown in FIG. 4 and retracts into the coil shape shown in FIGS. 2 and 9 in the retracted position.

When scalpel 10 is in the intermediate position shown in FIGS. 1 and 2, blade 100 is within open end 33 and surrounded by handle 30, and carriage 20 is then releasably latched in position by interaction between oblong shaped post 24 and second opening 42 which permits scalpel 10 to be stored or passed between users.

FIGS. 3-7 are an isometric view, a cross-sectional view, a top view and two side views, respectively, of the surgical scalpel shown in FIG. 1. More particularly, FIGS. 3 and 4 show the surgical scalpel in an extended position, wherein blade 100 extends beyond open end 33 of handle 30 in position to be used. FIG. 5 more clearly shows view port 41 in top surface 34 and post 24 extending from button 26 through slot 38.

When the scalpel is in the extended position shown in FIGS. 3 and 4, button 26 is rotated by the user so that post 24 securely latches within first opening 39 to prevent carriage 20 from moving with respect to handle 30. It is important to prevent carriage 20 and blade 100 from moving during use, since the position and orientation of blade 100 with respect to handle 30 is important when performing surgical procedures. If carriage 20 accidentally slides within handle 30 injury to the patient may occur. In addition, the present invention also uses the orientation of tab 27 on button 26 with respect to the longitudinal axis of handle 30 to provide the user with an indication as to whether carriage 20 is locked in position for use.

FIGS. 6 and 7 are side views of the surgical scalpel, with FIG. 7 showing the front portion of the surgical scalpel and the rotational operation of the button in the A direction, when locking and unlocking blade 100 in the extended position. As shown in FIGS. 6 and 7, post 24 on button 26 has an oblong shape. After scalpel 10 has been used and the user wishes to secure scalpel 10 for storage, passing to other personnel, or disposal, the user can rotate the oblong shaped post 24 on button 26 from the orientation shown in FIG. 7 to the orientation shown in FIG. 6 to release carriage 20. When carriage 20 has been released, carriage 20 can be slid by the user applying sufficient force on button 26 to remove shoulder 43 from first opening 39 and move carriage 20 in the direction of butt 32. Carriage 20 can then be moved from the extended position to the intermediate position shown in FIGS. 1 and 2 or to the permanently locked position shown in FIGS. 8 and 9, discussed below. However, if the oblong shaped post 24 has been rotated in first opening 39 to the orientation shown in FIG. 7, carriage 20 cannot be slid out of the extended position in which the scalpel is used. Of course, if oblong shaped post 24 is rotated in second opening 42, in the intermediate position, carriage 20 likewise cannot be slid from that position. When carriage 20 has been finally slid to the permanently locked position, shown in FIGS. 8 and 9 and discussed below, there is no need to rotate button 26 to lock carriage 20, since the means for permanently locking carriage 20 in that position is independent of the operation of button 26.

Figure 9:
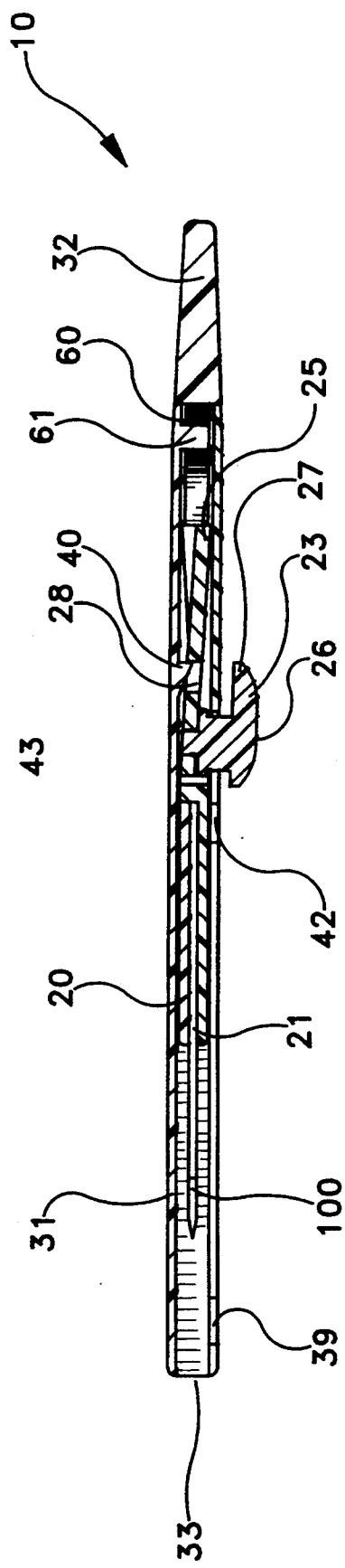
FIG. 9 is a cross-sectional view of the surgical scalpel shown in FIG. 8.
Figure 8:
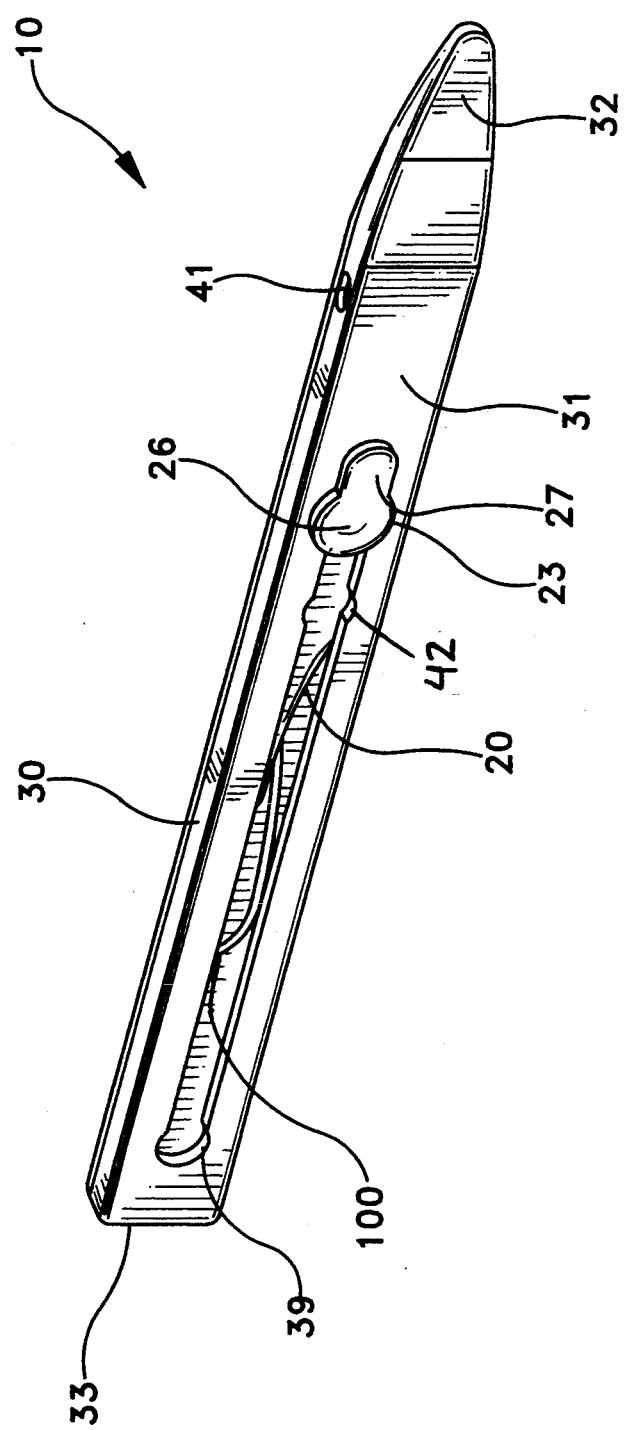
FIG. 8 is an isometric view of the surgical scalpel shown in FIG. 1, with the blade in a permanently locked retracted position.

FIGS. 8 and 9 are an isometric view and a cross-sectional view, respectively, of the surgical scalpel in a fully-retracted and permanently locked position for disposal. When surgical scalpel 10 is in the fully-retracted and permanently locked position, blade 100 is permanently surrounded by and locked within handle 30. In this position carriage 20 and handle 30 are permanently locked together by a locking mechanism, shown in FIG. 10 and discussed below.

FIG. 10 is an exploded isometric view of the surgical scalpel shown in FIGS. 1-9 that more clearly shows each component in scalpel 10, as discussed above, using the same reference numbers. In addition, FIG. 10 shows the locking mechanism used to lock carriage 20 in the locked position, the locking mechanism including a cleat 40 within handle 30 and a locking port 28 on carriage 20. As carriage 20 slides from the intermediate position shown in FIGS. 1 and 2, cleat 40 slides through a slot 29 in flexible portion 25 until it mates with and locks within locking port 28. Of course, after cleat 40 has latched to port 28, carriage 20 cannot be moved out of the locked position and scalpel 10 must then be disposed of.

The present invention also includes means for indicating whether scalpel 10 is or is not in the locked position shown in FIGS. 8 and 9. The indication means includes view port 41, shown in FIGS. 1, 3, 5, 8 and 10, and an indicator display 45, shown in FIG. 10. Indicator display 45 is seen through view port 41, when scalpel 10 is in the permanently locked retracted position shown in FIGS. 8 and 9. Preferably, if carriage 20 and blade 100 are permanently locked in the retracted position, a predetermined color, e.g., red, would appear in view port 41, otherwise the window would be empty or show another predetermined color, e.g., green or black.

Figure 11:
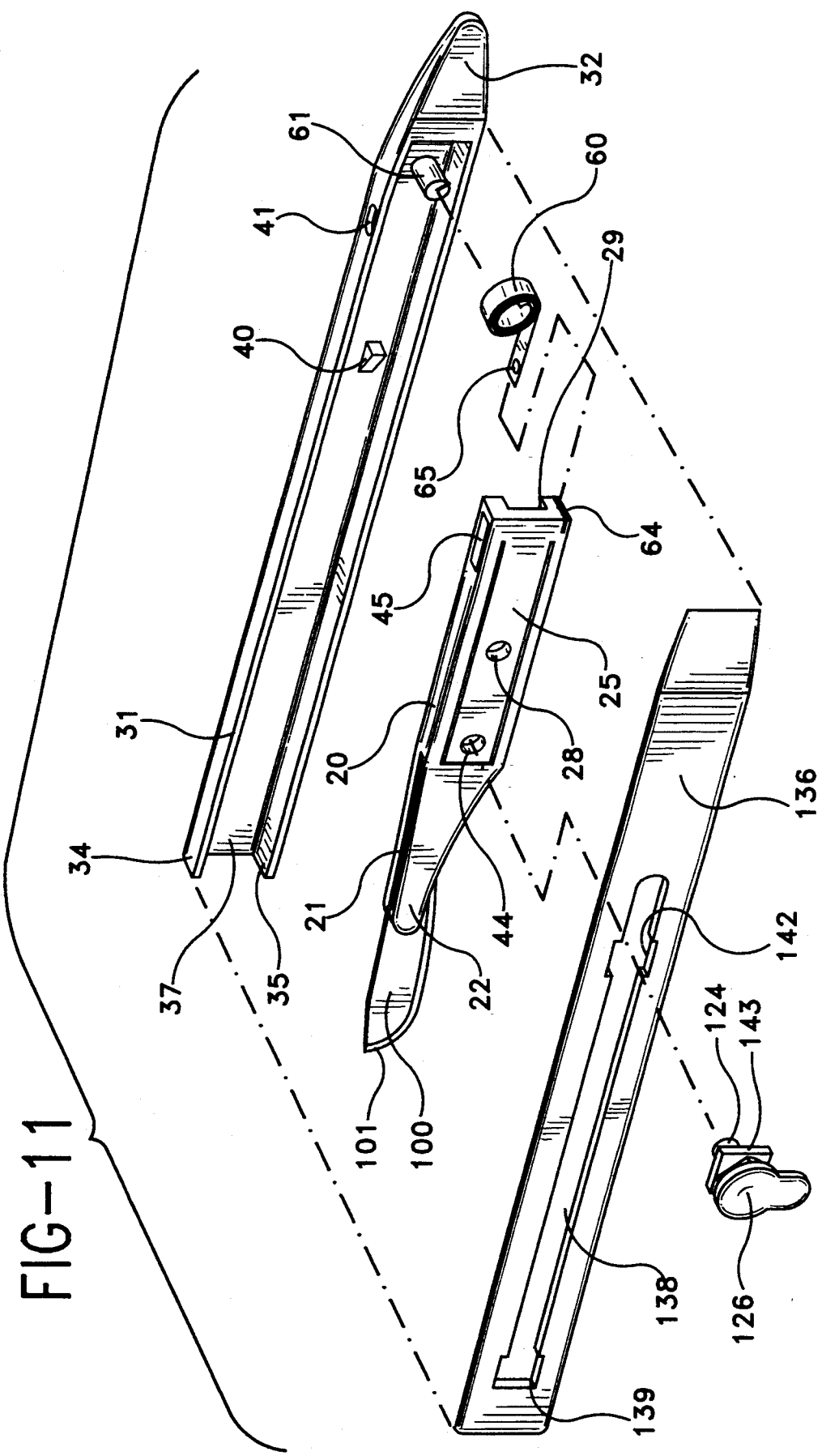
FIG. 11 is an exploded isometric view of another embodiment of the surgical scalpel shown in FIG. 1.

FIG. 11 is an exploded isometric view of an alternative embodiment of the surgical scalpel shown in FIG. 1, with similar components being identified by the same reference numerals. The scalpel in FIG. 11, however, includes a first side wall 136 having a slot 138 with a pair of square shaped holes 139 and 142 for receiving a square shoulder 143 on a button 126. Button 126 is fastened by a post 124 to port 44 in flexible portion 25 on carriage 20.

Accordingly, it will be appreciated that the present invention provides a much needed scalpel having a blade that is guarded from inadvertent contact before and after use with means for insuring that the blade will stay in the extended position during use, means for easily and permanently locking the blade in a position for disposal purposes, and means for indicating that the blade is permanently locked.

Both of the scalpels shown in FIGS. 1-11 can be made of surgical steel or plastic material. However, it would be preferable to make the entire scalpel 10, except for blade 100, in plastic for disposal purposes. In addition, it should be understood, of course, that the above-described embodiments are simply illustrative of apparatus embodying the principles and concepts of the present invention. Other suitable variations and modifications could be made to the apparatus described and still remain within the scope of the present invention.

What is claimed is:

1. A surgical scalpel comprising:
 a handle having a closed proximal end and an open distal end and defining a slot with sidewalls therein;
 a carriage slidably mounted within said handle to slide from a retracted position to an extended position;
 a blade mounted to said carriage; and
 a rotatable button having a shoulder connected to said carriage and extending through the slot wherein said shoulder engages the sidewalls of the slot when said rotatable button is rotated to hold said carriage in position with respect to said handle.

2. The surgical scalpel according to claim 1 further including a cleat within said handle and a locking port in said carriage, wherein said cleat mates with and locks to said locking port when said carriage is in a fully-retracted and locked position.

3. A surgical scalpel according to claim 2, further comprising means for indicating whether said carriage is in the fully-retracted and locked position.

4. A surgical scalpel according to claim 1, further comprising means for automatically retracting said carriage into the retracted position.

5. A surgical scalpel according to claim 4, wherein said means for automatically retracting said carriage into the retracted position includes a coil spring mounted between said handle and said carriage.

6. A surgical scalpel comprising:
a handle having a distal end and a view port therein;
a carriage slidably mounted in said handle to slide between a retracted position and an extended position, and finally to a fully-retracted and locked position for disposal and having an indicator display thereon which is visible through said view port when said carriage is in the fully-retracted and locked position; and
a blade attached to said carriage.

7. The surgical scalpel according to claim 6, wherein said indicator display is a predetermined color to indicate that said carriage is locked and safe for disposal.

8. A surgical scalpel according to claim 6, further comprising means for locking said carriage in a fully-retracted and locked position so that said blade is surrounded by said handle for disposal.

9. A surgical scalpel according to claim 8, wherein said locking means includes:
a cleat within said handle; and
a locking port in said carriage,
wherein said cleat mates with and locks to said locking port when said carriage is in the fully-retracted and locked position.

10. A surgical scalpel according to claim 6, further comprising means for latching said carriage in the retracted position, wherein said blade is surrounded by said shield and does not extend beyond said distal end of said handle.

11. A surgical scalpel according to claim 10, wherein said means for latching said carriage in position comprises:
a slot in said handle having an indent; and
a resilient button in said carriage having a shoulder extending therefrom,
wherein said shoulder engages said indent to latch said carriage in the position.

12. A surgical scalpel according to claim 11, further comprising means for securely latching said carriage in position by rotating said resilient button.

13. A surgical scalpel according to claim 6, further comprising means for automatically retracting said carriage into the retracted position.

14. A surgical scalpel comprising:
a handle having a distal end;
a carriage slidably mounted in said handle to slide between a retracted position and an extended position, and finally to a fully-retracted and locked position for disposal;
a blade attached to said carriage;
means for releasably latching said carriage in position to ensure that said carriage does not move during use;
means for indicating whether said carriage is in the fully-retracted and locked position; and
means for locking said carriage in a fully-retracted and locked position so that said blade is surrounded by said handle for disposal.

15. A surgical device comprising:
a handle having a closed proximal end, an open distal end and a cleat therein; and
a carriage having a locking port slidably mounted within said handle to slide from a retracted position to an extended position wherein said cleat mates with and locks to said locking port when said carriage is in the fully-retracted and locked position.

* * * * *